United States Patent
O'Keeffe

(10) Patent No.: US 9,445,784 B2
(45) Date of Patent: Sep. 20, 2016

(54) INTRAVASCULAR ULTRASOUND CATHETER

(75) Inventor: Daniel O'Keeffe, San Francisco, CA (US)

(73) Assignee: BOSTON SCIENTIFIC SCIMED, INC, Maple Grove, MN (US)

( * ) Notice: Subject to any disclaimer, the term of this patent is extended or adjusted under 35 U.S.C. 154(b) by 3460 days.

(21) Appl. No.: 11/233,216

(22) Filed: Sep. 22, 2005

(65) Prior Publication Data

US 2007/0066900 A1   Mar. 22, 2007

(51) Int. Cl.
| | | |
|---|---|---|
| *A61M 25/00* | (2006.01) | |
| *A61B 8/00* | (2006.01) | |
| *A61B 8/12* | (2006.01) | |
| *A61M 25/01* | (2006.01) | |

(52) U.S. Cl.
CPC ............... *A61B 8/445* (2013.01); *A61B 8/12* (2013.01); *A61M 25/0051* (2013.01); *A61M 25/0053* (2013.01); *A61M 25/0054* (2013.01); *A61M 25/0138* (2013.01)

(58) Field of Classification Search
USPC ......... 604/523–527, 264; 600/433–435, 585, 600/139–140, 143
See application file for complete search history.

(56) References Cited

U.S. PATENT DOCUMENTS

| | | |
|---|---|---|
| 1,060,665 A | 5/1913 | Bell |
| 2,441,166 A | 5/1948 | Raspert |
| 3,452,742 A | 7/1969 | Muller |
| 3,605,725 A | 9/1971 | Bentov |
| 3,625,200 A | 12/1971 | Muller |
| 3,811,449 A | 5/1974 | Gravlee et al. |
| 3,841,308 A | 10/1974 | Tate |
| 3,890,977 A | 6/1975 | Wilson |
| 4,003,369 A | 1/1977 | Heilman et al. |
| 4,020,829 A | 5/1977 | Willson et al. |
| 4,137,906 A | 2/1979 | Akiyama et al. |
| 4,215,703 A | 8/1980 | Willson |
| 4,425,919 A | 1/1984 | Alston, Jr. et al. |
| 4,456,017 A | 6/1984 | Miles |
| 4,503,569 A | 3/1985 | Dotter |
| 4,516,972 A | 5/1985 | Samson |
| 4,545,390 A | 10/1985 | Leary |
| 4,563,181 A | 1/1986 | Wijayarathna et al. |

(Continued)

FOREIGN PATENT DOCUMENTS

| | | |
|---|---|---|
| DE | 25 39 191 | 3/1976 |
| EP | 0 045 931 | 2/1982 |

(Continued)

OTHER PUBLICATIONS

"Mechanical Design and Systems Handbook", H.A. Rothbart, 1964, p. 33-13 (one sheet).

(Continued)

*Primary Examiner* — Tse Chen
*Assistant Examiner* — Patricia Park
(74) *Attorney, Agent, or Firm* — Lowe Graham Jones PLLC; Bruce E. Black

(57) ABSTRACT

An intravascular ultrasound catheter may include a central lumen adapted to receive a drive shaft bearing an ultrasound transducer. The intravascular ultrasound catheter may in some instances exhibit improved flexibility. The catheter can include an inner polymeric layer, an outer polymeric layer and a spiral-cut hypotube that is positioned between the inner polymeric layer and the outer polymeric layer.

22 Claims, 13 Drawing Sheets

(56) References Cited

U.S. PATENT DOCUMENTS

| | | |
|---|---|---|
| 4,580,551 A | 4/1986 | Siegmund et al. |
| 4,586,923 A | 5/1986 | Gould et al. |
| 4,655,214 A | 4/1987 | Linder |
| 4,665,906 A | 5/1987 | Jervis |
| 4,721,117 A | 1/1988 | Mar et al. |
| 4,737,153 A | 4/1988 | Shimamura et al. |
| 4,763,647 A | 8/1988 | Gambale |
| 4,781,186 A | 11/1988 | Simpson et al. |
| 4,794,931 A | 1/1989 | Yock |
| 4,800,890 A | 1/1989 | Cramer |
| 4,811,743 A | 3/1989 | Stevens |
| 4,813,434 A | 3/1989 | Buchbinder et al. |
| 4,815,478 A | 3/1989 | Buchbinder et al. |
| 4,827,941 A | 5/1989 | Taylor et al. |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,886,067 A | 12/1989 | Palermo |
| 4,911,148 A | 3/1990 | Sosnowski et al. |
| 4,917,102 A | 4/1990 | Miller et al. |
| 4,932,959 A | 6/1990 | Horzewski et al. |
| 4,934,380 A | 6/1990 | Toledo |
| 4,951,677 A | 8/1990 | Crowley et al. |
| 4,953,553 A | 9/1990 | Tremulis |
| 4,955,384 A | 9/1990 | Taylor et al. |
| 4,955,862 A | 9/1990 | Sepetka |
| 4,960,134 A | 10/1990 | Webster, Jr. |
| 4,960,410 A | 10/1990 | Pinchuk |
| 4,960,411 A | 10/1990 | Buchbinder |
| 4,964,409 A | 10/1990 | Tremulis |
| 4,966,163 A | 10/1990 | Kraus et al. |
| 4,976,688 A | 12/1990 | Rosenblum |
| 4,985,022 A | 1/1991 | Fearnot et al. |
| 4,989,608 A | 2/1991 | Ratner |
| 4,990,143 A | 2/1991 | Sheridan |
| 4,994,018 A | 2/1991 | Saper |
| 4,994,069 A | 2/1991 | Ritchart et al. |
| 4,998,923 A | 3/1991 | Samson et al. |
| 5,000,185 A | 3/1991 | Yock |
| 5,007,434 A | 4/1991 | Doyle et al. |
| 5,024,234 A | 6/1991 | Leary et al. |
| 5,037,404 A | 8/1991 | Gold et al. |
| 5,040,543 A | 8/1991 | Badera et al. |
| 5,042,985 A | 8/1991 | Elliott et al. |
| 5,049,130 A | 9/1991 | Powell |
| 5,052,404 A | 10/1991 | Hodgson |
| 5,063,935 A | 11/1991 | Gambale et al. |
| 5,095,915 A | 3/1992 | Engelson |
| 5,106,455 A | 4/1992 | Jacobsen et al. |
| 5,108,368 A | 4/1992 | Hammerslag et al. |
| 5,114,414 A | 5/1992 | Buchbinder |
| 5,125,395 A | 6/1992 | Adair |
| 5,125,895 A | 6/1992 | Buchbinder et al. |
| 5,144,959 A | 9/1992 | Gambale et al. |
| 5,147,317 A | 9/1992 | Shank et al. |
| 5,181,668 A | 1/1993 | Tsuji et al. |
| 5,190,050 A | 3/1993 | Nitzsche |
| 5,205,830 A | 4/1993 | Dassa et al. |
| 5,209,235 A | 5/1993 | Brisken et al. |
| 5,211,183 A | 5/1993 | Wilson |
| 5,217,482 A | 6/1993 | Keith |
| 5,238,004 A | 8/1993 | Sahatjian et al. |
| 5,242,396 A | 9/1993 | Evard |
| 5,242,441 A | 9/1993 | Avitall |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,259,393 A | 11/1993 | Corso, Jr. et al. |
| 5,267,979 A | 12/1993 | Appling et al. |
| 5,279,562 A | 1/1994 | Sirhan et al. |
| 5,295,493 A | 3/1994 | Radisch, Jr. |
| 5,300,032 A | 4/1994 | Hibbs et al. |
| 5,304,131 A | 4/1994 | Paskar |
| 5,304,134 A | 4/1994 | Kraus et al. |
| 5,306,252 A | 4/1994 | Yutori et al. |
| 5,313,949 A | 5/1994 | Yock |
| 5,314,408 A | 5/1994 | Salmon et al. |
| 5,315,996 A | 5/1994 | Lundquist |
| 5,318,525 A | 6/1994 | West et al. |
| 5,322,064 A | 6/1994 | Lundquist |
| 5,330,466 A | 7/1994 | Imran |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,353,798 A | 10/1994 | Sieben |
| 5,365,942 A | 11/1994 | Shank |
| 5,365,943 A | 11/1994 | Jansen |
| 5,368,564 A | 11/1994 | Savage |
| 5,372,138 A | 12/1994 | Crowley et al. |
| 5,376,077 A | 12/1994 | Gomringer |
| 5,376,084 A | 12/1994 | Bacich et al. |
| 5,399,164 A | 3/1995 | Snoke et al. |
| 5,406,960 A | 4/1995 | Corso, Jr. |
| 5,411,476 A | 5/1995 | Abrams |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,443,457 A | 8/1995 | Ginn et al. |
| 5,454,795 A | 10/1995 | Samson |
| 5,458,585 A | 10/1995 | Salmon et al. |
| 5,460,187 A | 10/1995 | Daigle et al. |
| 5,477,856 A | 12/1995 | Lundquist |
| 5,497,785 A | 3/1996 | Viera |
| 5,507,301 A | 4/1996 | Wasicek et al. |
| 5,507,725 A | 4/1996 | Savage et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,538,510 A | 7/1996 | Fontirroche et al. |
| 5,540,236 A | 7/1996 | Ginn |
| 5,542,924 A | 8/1996 | Snoke et al. |
| 5,546,948 A * | 8/1996 | Hamm et al. ................. 600/585 |
| 5,546,958 A | 8/1996 | Thorud et al. |
| 5,551,444 A | 9/1996 | Finlayson |
| 5,554,121 A | 9/1996 | Ainsworth et al. |
| 5,554,139 A | 9/1996 | Okajima |
| 5,562,619 A | 10/1996 | Mirarchi et al. |
| 5,569,197 A | 10/1996 | Helmus et al. |
| 5,569,200 A | 10/1996 | Umeno et al. |
| 5,569,218 A | 10/1996 | Berg |
| 5,571,073 A | 11/1996 | Castillo |
| 5,573,520 A | 11/1996 | Schwartz et al. |
| 5,584,821 A | 12/1996 | Hobbs et al. |
| 5,599,326 A | 2/1997 | Carter |
| 5,599,492 A | 2/1997 | Engelson |
| 5,601,539 A | 2/1997 | Corso, Jr. |
| 5,605,162 A | 2/1997 | Mirzaee et al. |
| 5,622,184 A | 4/1997 | Ashby et al. |
| 5,630,806 A | 5/1997 | Inagaki et al. |
| 5,637,089 A | 6/1997 | Abrams et al. |
| 5,643,209 A | 7/1997 | Fugoso et al. |
| 5,656,030 A | 8/1997 | Hunjan et al. |
| 5,658,264 A | 8/1997 | Samson et al. |
| 5,666,968 A | 9/1997 | Imran et al. |
| 5,666,969 A | 9/1997 | Urick et al. |
| 5,669,926 A | 9/1997 | Aust et al. |
| 5,676,659 A | 10/1997 | McGurk |
| 5,682,894 A | 11/1997 | Orr et al. |
| 5,685,312 A | 11/1997 | Yock |
| 5,690,120 A | 11/1997 | Jacobsen et al. |

(56) References Cited

U.S. PATENT DOCUMENTS

| | | |
|---|---|---|
| 5,715,817 A | 2/1998 | Stevens-Wright et al. |
| 5,715,825 A | 2/1998 | Crowley |
| 5,720,300 A | 2/1998 | Fagan et al. |
| 5,722,609 A | 3/1998 | Murakami |
| 5,728,063 A | 3/1998 | Preissman et al. |
| 5,741,429 A | 4/1998 | Donadio, III et al. |
| 5,746,701 A | 5/1998 | Noone |
| 5,769,819 A | 6/1998 | Schwab et al. |
| 5,769,830 A | 6/1998 | Parker |
| 5,771,895 A | 6/1998 | Slager |
| 5,772,609 A | 6/1998 | Nguyen et al. |
| 5,788,654 A | 8/1998 | Schwager |
| 5,788,707 A | 8/1998 | Del Toro et al. |
| 5,792,124 A | 8/1998 | Horrigan et al. |
| 5,797,856 A | 8/1998 | Frisbie et al. |
| 5,800,454 A | 9/1998 | Jacobsen et al. |
| 5,807,075 A | 9/1998 | Jacobsen et al. |
| 5,807,249 A | 9/1998 | Qin et al. |
| 5,820,594 A | 10/1998 | Fontirroche et al. |
| 5,824,173 A | 10/1998 | Fontirroche et al. |
| 5,827,225 A | 10/1998 | Ma Schwab |
| 5,827,242 A | 10/1998 | Follmer et al. |
| 5,833,632 A | 11/1998 | Jacobsen et al. |
| 5,836,926 A | 11/1998 | Peterson et al. |
| 5,842,994 A | 12/1998 | TenHoff et al. |
| 5,843,050 A | 12/1998 | Jones et al. |
| 5,843,244 A | 12/1998 | Pelton et al. |
| 5,851,203 A | 12/1998 | van Muiden |
| 5,897,537 A | 4/1999 | Berg et al. |
| 5,902,245 A | 5/1999 | Yock |
| 5,902,254 A | 5/1999 | Magram |
| 5,902,290 A | 5/1999 | Peacock, III et al. |
| 5,904,657 A | 5/1999 | Unsworth et al. |
| 5,906,590 A | 5/1999 | Hunjan et al. |
| 5,906,618 A | 5/1999 | Larson, III |
| 5,911,715 A | 6/1999 | Berg et al. |
| 5,911,717 A | 6/1999 | Jacobsen et al. |
| 5,916,177 A | 6/1999 | Schwager |
| 5,916,178 A | 6/1999 | Noone |
| 5,916,194 A | 6/1999 | Jacobsen et al. |
| 5,928,191 A | 7/1999 | Houser et al. |
| 5,931,830 A | 8/1999 | Jacobsen et al. |
| 5,935,108 A | 8/1999 | Katoh et al. |
| 5,944,689 A | 8/1999 | Houser et al. |
| 5,951,539 A | 9/1999 | Nita et al. |
| 5,957,941 A | 9/1999 | Ream |
| 5,971,975 A | 10/1999 | Mills et al. |
| 6,001,068 A | 12/1999 | Uchino et al. |
| 6,004,279 A | 12/1999 | Crowley et al. |
| 6,010,521 A | 1/2000 | Lee et al. |
| 6,013,052 A | 1/2000 | Durman et al. |
| 6,014,919 A | 1/2000 | Jacobsen et al. |
| 6,017,319 A | 1/2000 | Jacobsen et al. |
| 6,022,369 A | 2/2000 | Jacobsen et al. |
| 6,024,730 A | 2/2000 | Pagan |
| 6,027,461 A | 2/2000 | Walker et al. |
| 6,036,670 A | 3/2000 | Wijeratne et al. |
| 6,045,547 A | 4/2000 | Ren et al. |
| 6,048,338 A | 4/2000 | Larson et al. |
| 6,048,339 A | 4/2000 | Zirps et al. |
| 6,063,101 A | 5/2000 | Jacobsen et al. |
| 6,063,200 A | 5/2000 | Jacobsen et al. |
| 6,066,125 A | 5/2000 | Webster, Jr. |
| 6,066,361 A | 5/2000 | Jacobsen et al. |
| 6,106,485 A | 8/2000 | McMahon |
| 6,106,488 A | 8/2000 | Fleming et al. |
| 6,106,518 A | 8/2000 | Wittenberger et al. |
| 6,123,699 A | 9/2000 | Webster, Jr. |
| 6,139,510 A | 10/2000 | Palermo |
| 6,165,292 A | 12/2000 | Abrams et al. |
| 6,171,277 B1 | 1/2001 | Ponzi |
| 6,171,296 B1 | 1/2001 | Chow |
| 6,183,410 B1 | 2/2001 | Jacobsen et al. |
| 6,183,435 B1 | 2/2001 | Bumbalough et al. |
| 6,183,463 B1 | 2/2001 | Webster, Jr. |
| 6,193,686 B1 | 2/2001 | Estrada et al. |
| 6,198,974 B1 | 3/2001 | Webster, Jr. |
| 6,210,407 B1 | 4/2001 | Webster |
| 6,214,042 B1 | 4/2001 | Jacobsen et al. |
| 6,228,073 B1 | 5/2001 | Noone et al. |
| 6,251,092 B1 | 6/2001 | Qin et al. |
| 6,254,568 B1 | 7/2001 | Ponzi |
| 6,254,588 B1 | 7/2001 | Jones et al. |
| 6,258,080 B1 | 7/2001 | Samson |
| 6,260,458 B1 | 7/2001 | Jacobsen et al. |
| 6,267,746 B1 | 7/2001 | Bumbalough |
| 6,273,404 B1 | 8/2001 | Holman et al. |
| 6,273,876 B1 | 8/2001 | Klima et al. |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,319,248 B1 | 11/2001 | Nahon |
| 6,325,790 B1 | 12/2001 | Trotta |
| 6,332,880 B1 | 12/2001 | Yang et al. |
| 6,338,725 B1 | 1/2002 | Hermann et al. |
| 6,346,091 B1 | 2/2002 | Jacobsen et al. |
| 6,346,099 B1 | 2/2002 | Altman |
| 6,352,515 B1 | 3/2002 | Anderson et al. |
| 6,355,027 B1 | 3/2002 | Le et al. |
| 6,364,840 B1 | 4/2002 | Crowley |
| 6,368,301 B1 | 4/2002 | Hamilton et al. |
| 6,368,315 B1 | 4/2002 | Gillis et al. |
| 6,368,316 B1 | 4/2002 | Jansen et al. |
| 6,379,369 B1 | 4/2002 | Abrams et al. |
| 6,387,075 B1 | 5/2002 | Stivland et al. |
| 6,390,993 B1 | 5/2002 | Cornish et al. |
| 6,398,758 B1 | 6/2002 | Jacobsen et al. |
| 6,413,234 B1 | 7/2002 | Thompson et al. |
| 6,428,489 B1 | 8/2002 | Jacobsen et al. |
| 6,428,512 B1 | 8/2002 | Anderson et al. |
| 6,431,039 B1 | 8/2002 | Jacobsen et al. |
| 6,440,088 B1 | 8/2002 | Jacobsen |
| 6,440,126 B1 | 8/2002 | Abboud et al. |
| 6,468,260 B1 | 10/2002 | Bumbalough et al. |
| 6,478,778 B1 | 11/2002 | Jacobsen et al. |
| 6,482,217 B1 * | 11/2002 | Pintor et al. ............... 606/159 |
| 6,485,455 B1 | 11/2002 | Thompson et al. |
| 6,488,637 B1 | 12/2002 | Eder et al. |
| 6,491,648 B1 | 12/2002 | Cornish et al. |
| 6,491,671 B1 | 12/2002 | Larson, III et al. |
| 6,500,167 B1 | 12/2002 | Webster, Jr. |
| 6,508,803 B1 | 1/2003 | Horikawa et al. |
| 6,522,933 B2 | 2/2003 | Nguyen |
| 6,524,301 B1 | 2/2003 | Wilson et al. |
| 6,530,934 B1 | 3/2003 | Jacobsen et al. |
| 6,533,754 B1 | 3/2003 | Hisamatsu et al. |
| 6,540,725 B1 | 4/2003 | Ponzi |
| 6,547,779 B2 | 4/2003 | Levine et al. |
| 6,551,271 B2 | 4/2003 | Nguyen |
| 6,553,880 B2 | 4/2003 | Jacobsen et al. |
| 6,569,114 B2 | 5/2003 | Ponzi et al. |
| 6,571,131 B1 | 5/2003 | Nguyen |
| 6,572,553 B2 * | 6/2003 | Crowley ....................... 600/463 |
| 6,579,246 B2 | 6/2003 | Jacobsen et al. |
| 6,579,278 B1 | 6/2003 | Bencini |
| 6,585,717 B1 | 7/2003 | Wittenberger et al. |
| 6,585,718 B2 | 7/2003 | Hayzelden et al. |
| 6,592,520 B1 | 7/2003 | Peszynski et al. |
| 6,602,278 B1 | 8/2003 | Thompson et al. |
| 6,602,280 B2 | 8/2003 | Chobotov |
| 6,605,086 B2 | 8/2003 | Hayzelden et al. |
| 6,607,505 B1 | 8/2003 | Thompson et al. |
| 6,610,046 B1 * | 8/2003 | Usami et al. ................. 604/530 |
| 6,610,058 B2 | 8/2003 | Flores |
| 6,623,452 B2 * | 9/2003 | Chien et al. ............. 604/103.01 |
| 6,652,508 B2 | 11/2003 | Griffin et al. ................. 604/526 |
| 6,682,493 B2 | 1/2004 | Mirigian |
| 6,730,095 B2 | 5/2004 | Olson, Jr. et al. |
| 6,777,644 B2 | 8/2004 | Peacock, III et al. |
| 6,918,882 B2 | 7/2005 | Skujins et al. |
| 6,997,937 B2 | 2/2006 | Jacobsen et al. |
| 7,815,599 B2 * | 10/2010 | Griffin et al. ................ 604/96.01 |
| 2001/0025075 A1 | 9/2001 | Smith et al. |

(56) References Cited

U.S. PATENT DOCUMENTS

| | | | |
|---|---|---|---|
| 2002/0010475 A1 | 1/2002 | Lui | |
| 2002/0019599 A1 | 2/2002 | Rooney et al. | |
| 2002/0025998 A1 | 2/2002 | McCullough et al. | |
| 2003/0009208 A1 | 1/2003 | Snyder et al. | |
| 2003/0060732 A1 | 3/2003 | Jacobsen et al. | |
| 2003/0069521 A1 | 4/2003 | Reynolds et al. | |
| 2003/0069522 A1 | 4/2003 | Jacobsen et al. | |
| 2004/0176740 A1* | 9/2004 | Chouinard | 604/527 |
| 2005/0283179 A1 | 12/2005 | Lentz | |
| 2005/0288628 A1* | 12/2005 | Jordan et al. | 604/96.01 |
| 2006/0030835 A1* | 2/2006 | Sherman et al. | 604/526 |
| 2007/0016054 A1* | 1/2007 | Cao et al. | 600/459 |

FOREIGN PATENT DOCUMENTS

| | | | |
|---|---|---|---|
| EP | 0 069 522 | 1/1983 | |
| EP | 0 087 933 | 9/1983 | |
| EP | 0 111 044 | 6/1984 | |
| EP | 0 181 174 | 5/1986 | |
| EP | 0 521 595 | 1/1993 | |
| EP | 0 608 853 | 8/1994 | |
| EP | 0608853 * | 8/1994 | A61M 29/20 |
| EP | 0 778 038 | 6/1997 | |
| EP | 0 778 039 | 6/1997 | |
| EP | 0 778 040 | 6/1997 | |
| EP | 0 790 066 | 8/1997 | |
| EP | 0 812 599 | 12/1997 | |
| EP | 0 865 772 | 9/1998 | |
| EP | 0 865 773 | 9/1998 | |
| EP | 0 917 885 | 5/1999 | |
| EP | 0 935 947 | 8/1999 | |
| EP | 0 937 481 | 8/1999 | |
| JP | 7-51067 Y2 | 12/1991 | |
| JP | 7-28562 U | 5/1995 | |
| JP | 10-118193 | 5/1998 | |
| WO | WO 92/04072 | 3/1992 | |
| WO | WO 92/07619 | 5/1992 | |
| WO | WO 93/04722 | 3/1993 | |
| WO | WO 95/24236 | 9/1995 | |
| WO | WO 96/19255 | 6/1996 | |
| WO | WO 97/43949 | 11/1997 | |
| WO | WO 97/44083 | 11/1997 | |
| WO | WO 97/44086 | 11/1997 | |
| WO | WO 98/10694 | 3/1998 | |
| WO | WO 99/11313 | 3/1999 | |
| WO | WO 00/27303 | 5/2000 | |
| WO | WO 00/30710 | 6/2000 | |
| WO | WO 00/48645 | 8/2000 | |
| WO | WO 00/57943 | 10/2000 | |
| WO | WO 00/66199 | 11/2000 | |
| WO | WO 00/67845 | 11/2000 | |
| WO | WO 00/72907 | 12/2000 | |
| WO | WO 01/28620 | 4/2001 | |
| WO | WO 01/45773 | 6/2001 | |
| WO | WO 01/93920 | 12/2001 | |
| WO | WO 02/13682 | 2/2002 | |
| WO | WO 03/004086 | 1/2003 | |

OTHER PUBLICATIONS

Office Action mailed Aug. 10, 2006 for U.S. Appl. No. 10/869,996, filed Jun. 17, 2004.

Office Action mailed May 2, 2007 for U.S. Appl. No. 10/869,996, filed Jun. 17, 2004.

Office Action mailed Jun. 22, 2009 for U.S. Appl. No. 10/869,996, filed Jun. 17, 2004.

* cited by examiner

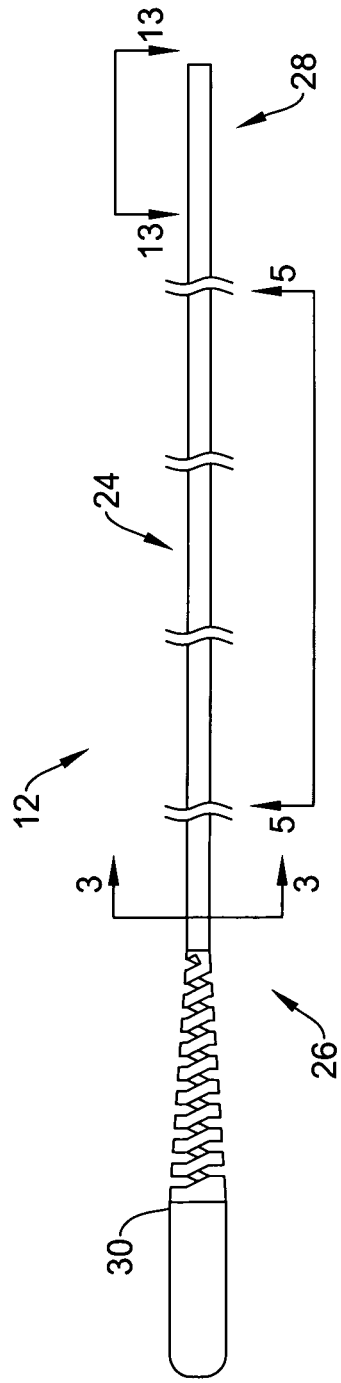
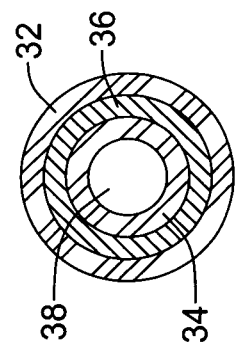
Figure 2
Figure 3

INTRAVASCULAR ULTRASOUND CATHETER

TECHNICAL FIELD

The invention relates generally to catheters and more particularly to intravascular ultrasound catheters.

BACKGROUND

Ultrasound can be useful in a variety of medical procedures. Intravascular ultrasound, in which an ultrasound transducer is advanced into a patient's body through the patient's vasculature, has particular uses and advantages.

An ultrasound transducer can be advanced through a patient's vasculature within an ultrasound catheter. While ultrasound catheters are known, a need remains for improved ultrasound catheters. A need remains as well for ultrasound catheters exhibiting improved flexibility.

SUMMARY

The present invention pertains to catheters such as intravascular ultrasound catheters. An intravascular ultrasound catheter may include a central lumen adapted to receive a drive shaft bearing an ultrasound transducer. The intravascular ultrasound catheter may, in some instances, exhibit improved flexibility.

Accordingly, an example embodiment of the present invention can be found in an intravascular ultrasound catheter that has a distal portion and a proximal portion. The catheter can include an inner polymeric layer, an outer polymeric layer and a spiral-cut hypotube that is positioned between the inner polymeric layer and the outer polymeric layer and that extends from the distal portion of the catheter to the proximal portion.

The spiral-cut hypotube has a pitch having a rate of change, i.e., a first derivative, that is a function of distance from a distal end of the spiral-cut hypotube. In other words, the pitch, or inches per turn, changes at a rate that depends upon relative position along the hypotube. At one point on the hypotube, the pitch can change slowly with respect to position while at a point positioned elsewhere on the hypotube, the pitch can change more rapidly with respect to position.

Another example embodiment of the present invention can be found in an intravascular ultrasound assembly that includes an intravascular ultrasound drive shaft having a distal end and an ultrasound transducer positioned near the distal end of the intravascular ultrasound drive shaft. The assembly also includes a catheter that is adapted to receive the intravascular ultrasound drive shaft.

The catheter has an inner polymeric layer that defines a lumen that is adapted to accommodate the intravascular ultrasound drive shaft. The catheter includes an outer polymeric layer and a spiral-cut hypotube that extends between the inner polymeric layer and the outer polymeric layer from a distal portion to a proximal portion of the catheter.

The above summary of the present invention is not intended to describe each disclosed embodiment or every implementation of the present invention. The Figures, Detailed Description and Examples which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 2 is a schematic illustration of an intravascular ultrasound catheter in accordance with an embodiment of the invention;

FIG. 3 is a cross-section taken along line 3-3 of FIG. 2;

Figure 1:
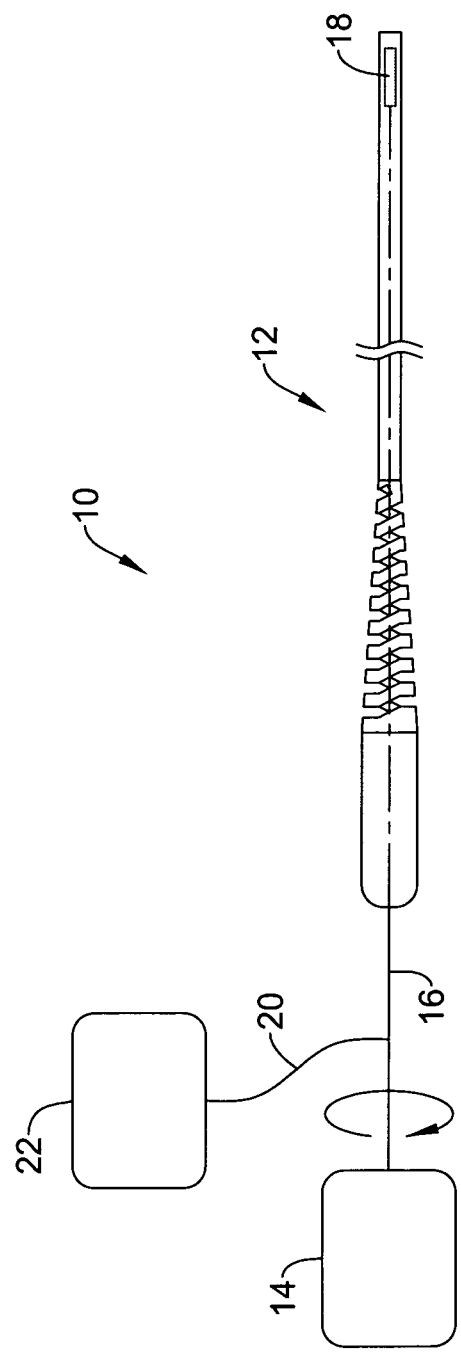
FIG. 1 is a schematic illustration of an intravascular ultrasound assembly in accordance with an embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value, i.e., having the same function or result. In many instances, the term "about" may include numbers that are rounded to the nearest significant figure.

As used in this specification and in the appended claims, the singular forms "a", "an", and "the" include plural referents unless the content clearly dictates otherwise. As used in this specification and in the appended claims, the term "or" is generally employed in its sense including "and/or" unless the content clearly dictates otherwise.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

FIG. 1 illustrates an intravascular ultrasound assembly 10 in accordance with an embodiment of the invention. The intravascular ultrasound assembly 10 includes an intravascular ultrasound catheter 12. A motor 14 rotates a drive shaft 16 that extends through the intravascular ultrasound catheter 12. An ultrasound transducer 18 is positioned at the distal end of the intravascular ultrasound catheter 12. The drive shaft 16 can include one or more wires 20 for carrying a signal from the ultrasound transducer 18 to a monitor 22.

Several of these components can include elements known in the art. For example, the motor 14 can be any suitable electrically driven motor having an appropriate speed and load rating. The drive shaft 16 can be formed from any suitable material or materials. The ultrasound transducer 18 may be any suitable transducer crystal made from any suitable material such as a barium titanate, a lead zirconate titanate, a lead metaniobate, and others. The monitor 22 can simply be a display unit such as a cathode ray tube or an LCD display. In some instances, the monitor 22 can represent a computer system including data processing systems as well as a display unit.

The intravascular ultrasound catheter 12 can be discussed in greater detail with respect to FIG. 2. In the illustrated embodiment, the intravascular ultrasound catheter 12 includes an elongate shaft 24 that has a proximal end 26 and a distal end 28. A hub and strain relief assembly 30 can be connected to or disposed about the proximal end 26 of the elongate shaft 24. The hub and strain relief assembly 30 can be of conventional design and can be attached using conventional techniques. The intravascular ultrasound catheter 12 can be sized in accordance with its intended use. The catheter 12 can have a length that is in the range of about 50 to about 200 centimeters and can have a diameter that is in the range of about 1.7 F (French), but can be as large as about 12 F for certain applications.

FIG. 3 is a cross-sectional view of the elongate shaft 24, taken along line 3-3 of FIG. 2, and illustrates a portion of elongate shaft 24. In particular, elongate shaft 24 includes an outer polymer layer 32, and inner polymer layer 34, and an intermediate metallic layer 36. In some embodiments, the intermediate metallic layer 36 can be a hypotube. A lumen 38 is defined by the inner polymer layer 34 and extends through the elongate shaft 24. The lumen 38 can in, some instances, be adapted to accommodate an intravascular ultrasound drive shaft 16 (as illustrated in FIG. 1). In particular, the lumen 38 may provide a smooth, low-friction surface for the drive shaft 16.

In some embodiments, the inner polymer layer 34 can be formed of or include a coating of a material having a suitably low coefficient of friction. Examples of suitable materials include polytetrafluoroethylene (PTFE), better known as TEFLON®. The inner polymer layer 34 can be dimensioned to define a lumen 38 having an appropriate inner diameter to accommodate its intended use. In some embodiments, the inner polymer layer 34 can define a lumen 38 having a diameter of about 0.020 inches and can have a wall thickness of about 0.001 inches.

The outer polymer layer 32 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX®), silicones, and co-polymers. The outer polymer layer 32 can be a single polymer, multiple longitudinal sections or layers, or a blend of polymers. By employing careful selection of materials and processing techniques, thermoplastic, solvent soluble, and thermosetting variants of these materials can be employed to achieve the desired results.

While not expressly illustrated, it is contemplated that the elongate shaft 24 may include several different sections that can vary in flexibility. In some instances, for example, the inner polymer layer 34 and perhaps the intermediate metallic layer 36 may extend continuously at least substantially the entire length of the elongate shaft 12. The outer polymer layer 32, however, may have several sections formed of differing polymers to provide additional flexibility. For example, the outer polymer layer 32 may include (not illustrated) a proximal section, a middle section and a distal section. The distal section may be formed of a polymer having a lower durometer than that of the middle section, which may itself be formed of a polymer having a lower durometer than that of the proximal section.

In particular embodiments, a thermoplastic polymer such as a co-polyester thermoplastic elastomer, for example, that available commercially under the ARNITEL® name, can be used. The outer polymer layer 32 can have an inner diameter that is about equal to the outer diameter of the inner polymer layer 34. The outer layer 32 can have an inner diameter that is slightly greater than the outer diameter of the inner polymer layer 34 to accommodate the thickness of the intermediate metallic layer 36. In some embodiments, the outer polymer layer 32 of the shaft can have an inner diameter in the range of about 0.025 inches to about 0.100 inches and an outer diameter in the range of about 0.028 inches to about 0.150 inches.

The outer polymer layer 32 may in, some instances, provide a compressive force to the intermediate metallic layer 36 in order to help retain a desired tubular shape for the intermediate metallic layer 36. In some cases, the outer polymer layer 32 may have a compression fit over the intermediate metallic layer 36. In some instances, the outer polymer layer 32 may have an interference fit or a slip fit with the intermediate metallic layer 36.

Figure 4:
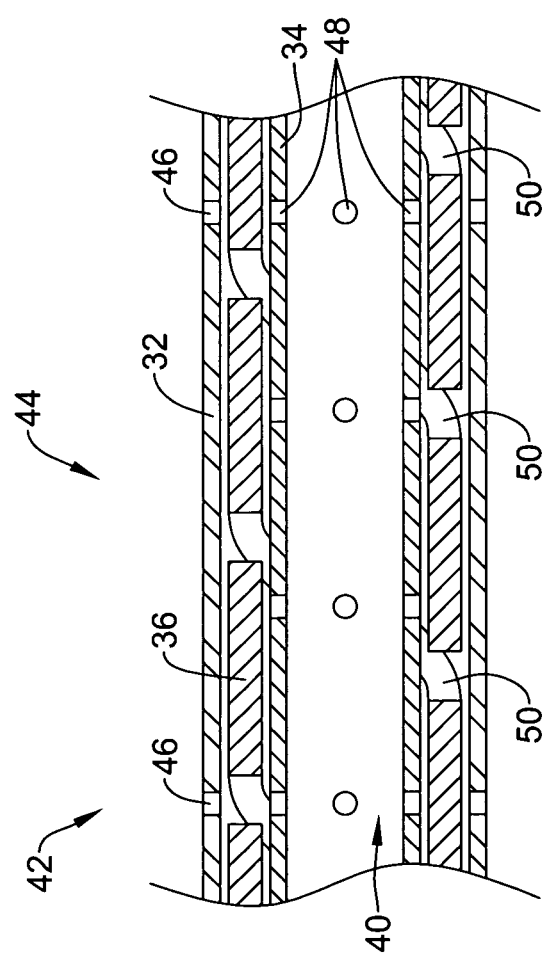
FIG. 4 is a diagrammatic longitudinal cross-section representing a particular embodiment of a portion of the intravascular ultrasound catheter of FIG. 2.

In some instances, it may be useful to be able to provide fluid from an interior of the catheter 12 to the exterior of the catheter 12. FIG. 4 is a diagrammatic partial cross-section of a portion of the catheter 12 illustrating optional features. This particular cross-section may represent a cross-section through any particular section of the catheter 12 and will be referenced as catheter section 44. FIG. 4 illustrates an embodiment in which fluid may pass from an interior 40 of catheter section 44 to an exterior 42 of catheter section 44. In some instances, it may be useful to, for example, hydrate an exterior portion of the catheter 12 prior to or during use. Alternatively, it may be useful to provide fluid from an interior of the catheter 12 to surround the intermediate metallic layer and the inner surface of the outer polymer layer.

As discussed above, catheter section 44 includes an outer polymer layer 32, an inner polymer layer 34 and an intermediate metallic layer 36, much as discussed with respect to FIGS. 1-3. In FIG. 4, however, catheter section 44 includes one or more apertures 46 provided within the outer polymer layer 32 and one or more apertures 48 provided within the inner polymer layer 34. It can be seen that the apertures 46 and the apertures 48 may be aligned with spiral-cuts or kerfs 50 which can be machined within the intermediate metallic layer 36. Consequently, fluid may pass from the interior 40, through apertures 48, into kerfs 50, and through apertures 46. In an alternative embodiment, the apertures 46 can be omitted which would allow fluid to flow into the area including the intermediate metallic layer.

Figure 5:
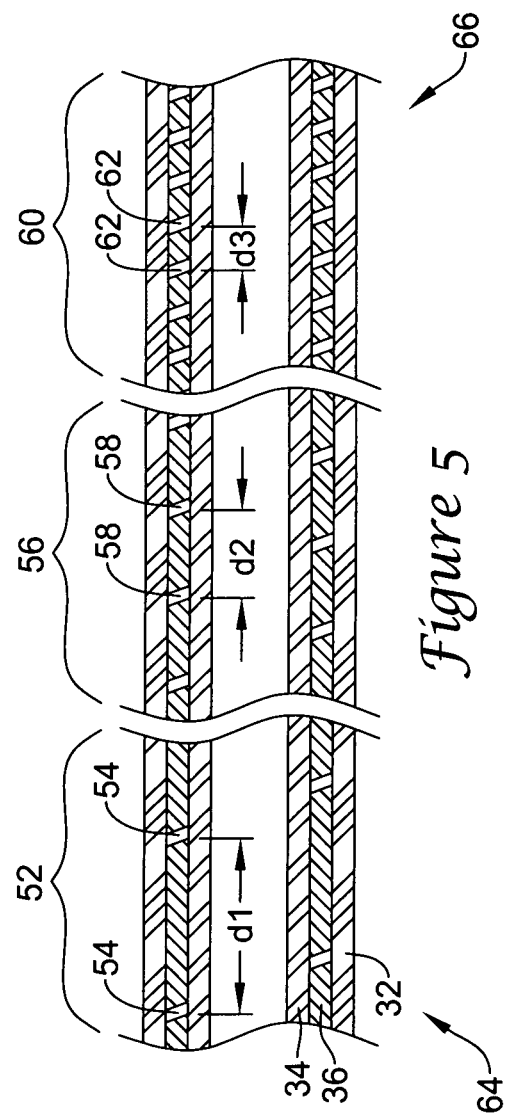
FIG. 5 is a longitudinal cross-section taken along line 5-5 of FIG. 2.

FIG. 5 is a longitudinal cross-section taken along line 5-5 of FIG. 2. FIG. 5 shows that, as with respect to FIG. 3, the elongate shaft 24 includes the outer polymer layer 32, the inner polymer layer 34 and the intermediate metallic layer 36. In some instances, the intermediate metallic layer 36 may include or be formed from a metal hypotube that has been spirally cut for flexibility. The elongate shaft 24 can include a first portion 52 having (as illustrated) two spiral-cuts 54. The first portion 52 corresponds to a (relatively) proximal portion 64. In the first portion 52, it can be seen that adjacent spiral-cuts 54 are spaced a distance d1 apart.

The elongate shaft 24 includes a second portion 56 having (as illustrated) four spiral-cuts 58 as an example and corresponds to an intermediate portion. It can be seen that adjacent spiral-cuts 58 are spaced a distance d2 apart, and that d2 is less than d1. The elongate shaft 24 also includes a third portion 60 having (as illustrated) seven spiral-cuts 62 as an example. It can be seen that adjacent spiral-cuts 62 are spaced a distance d3 apart, and that d3 is less than d2. The third portion 60 corresponds to a (relatively) distal portion 66. The number of cuts and distance apart can, however, be varied within the scope of the present invention.

In some embodiments, the pitch, or the spacing between adjacent turnings or windings, may decrease considerably when moving from the proximal end 26 of the elongate shaft 24 to the distal end 28 of the elongate shaft 24. In some embodiments, the intermediate metallic layer 36 may be spiral-cut from the proximal end 26 to the distal end 28. In some instances, the intermediate metallic layer 36 may be spiral-cut from a position distal of the proximal end 26 to the distal end 28. In particular, the intermediate metallic layer 36 may be spiral-cut from about a midpoint of the elongate shaft 24 to the distal end 28, although other points along the shaft may be selected.

In some instances, the intermediate metallic layer 36 may be spiral-cut such that adjacent windings or kerfs are very close together near the distal end 28 of the elongate shaft and are substantially less close together as distance from the distal end 28 increases. To illustrate, adjacent windings or kerfs may be spaced apart from 0.005 to about 0.25 inches at the distal end 28 while being spaced about 0.2 to about 1.0 inches at an opposite, more proximal, end of the spiral cutting. As noted above, the spiral-cutting need not extend all the way to the proximal end 26 of the elongate shaft 24.

By cutting the intermediate metallic layer 36 in this fashion, the intravascular ultrasound catheter 12 may have a flexibility that is much greater near the distal end 28 than at positions proximal to the distal end 28. The intermediate metallic layer 36 may be cut in any suitable fashion. In a particular embodiment, the intermediate metallic layer 36 is spiral-cut by a computer-guided laser.

In particular embodiments, the pitch may be given by an equation defining the pitch in terms of a distance to the distal end 28 of the elongate shaft 24. The pitch may have a rate of change, or first derivative in calculus terms, that is itself a function of relative position. As a result, the rate at which the pitch changes will itself vary as one moves from the proximal end 26 to the distal end 28.

In some instances, the pitch may decrease exponentially when moving toward the distal end 28. In some embodiments, the pitch may be given by the formula $y=A^{(Bx)}+C$, where y is the pitch, x is the distance from the distal end of the elongate shaft 24, A is in a range of about 5 to about 100, B is in a range of about 0.01 to about 1, and C is in a range of about 0 to about 25.

Figure 6:
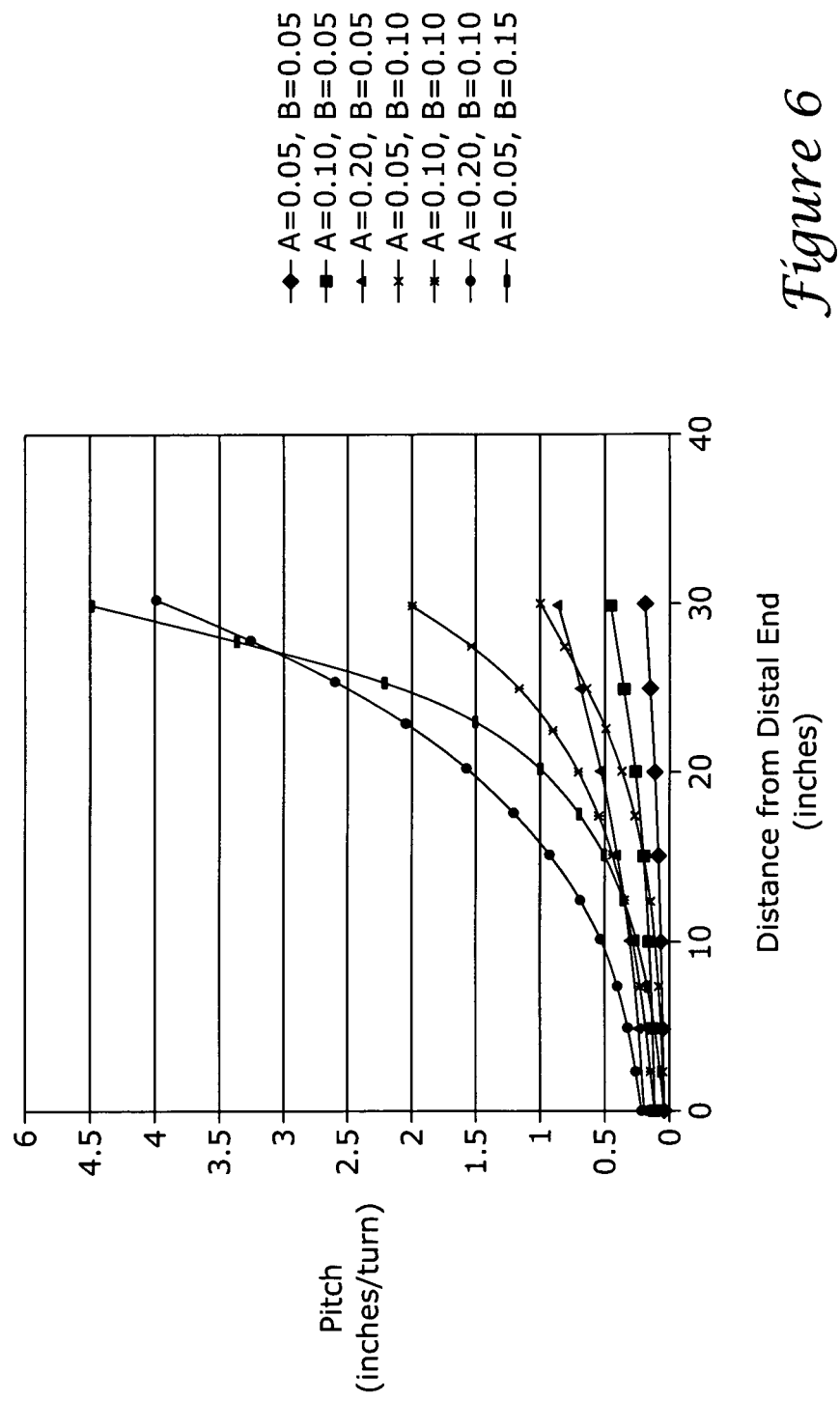
FIG. 6 is a graphical representation illustrating examples of exponentially decaying pitch in accordance with an embodiment of the invention.

FIG. 6 illustrates several possible exponential pitches in which A varies from 0.05 to 0.20, B varies from 0.05 to 0.10, and C is set equal to zero. It can be seen that the pitch, or inches per turn, increases rapidly in moving from the distal end to the proximal end of the intermediate metallic layer 36.

Figure 7:
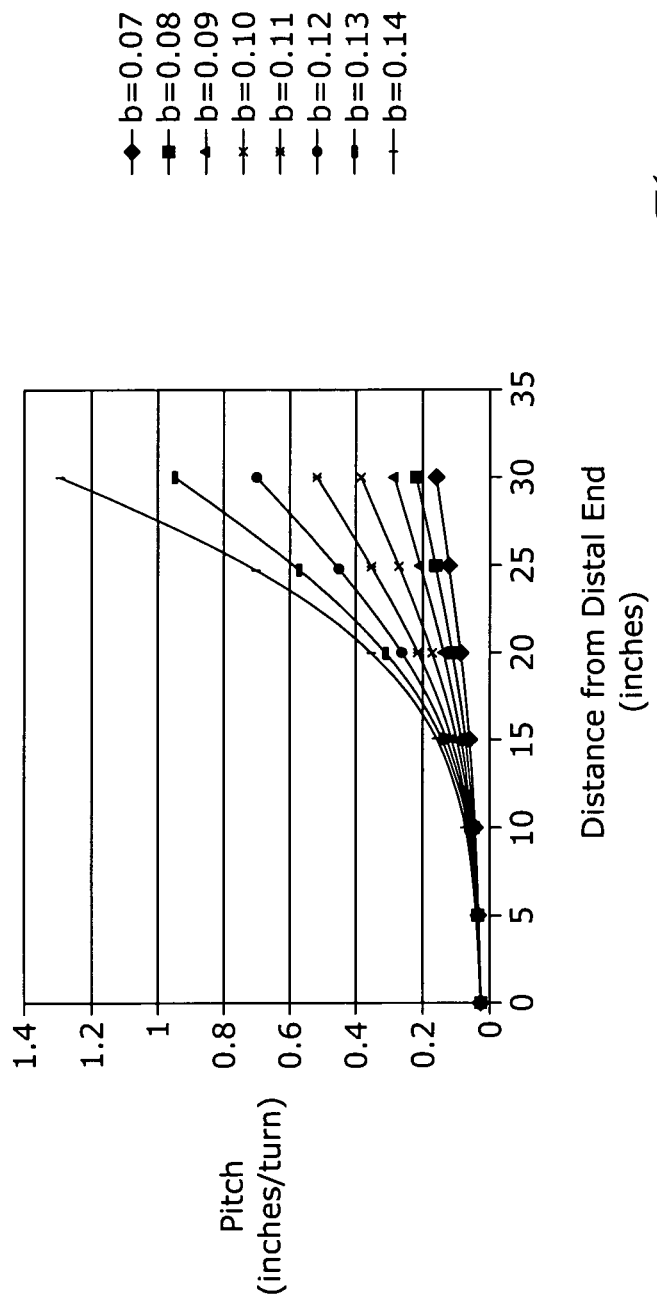
FIG. 7 is a graphical representation illustrating examples of exponentially decaying pitch in accordance with an embodiment of the invention.
Figure 8:
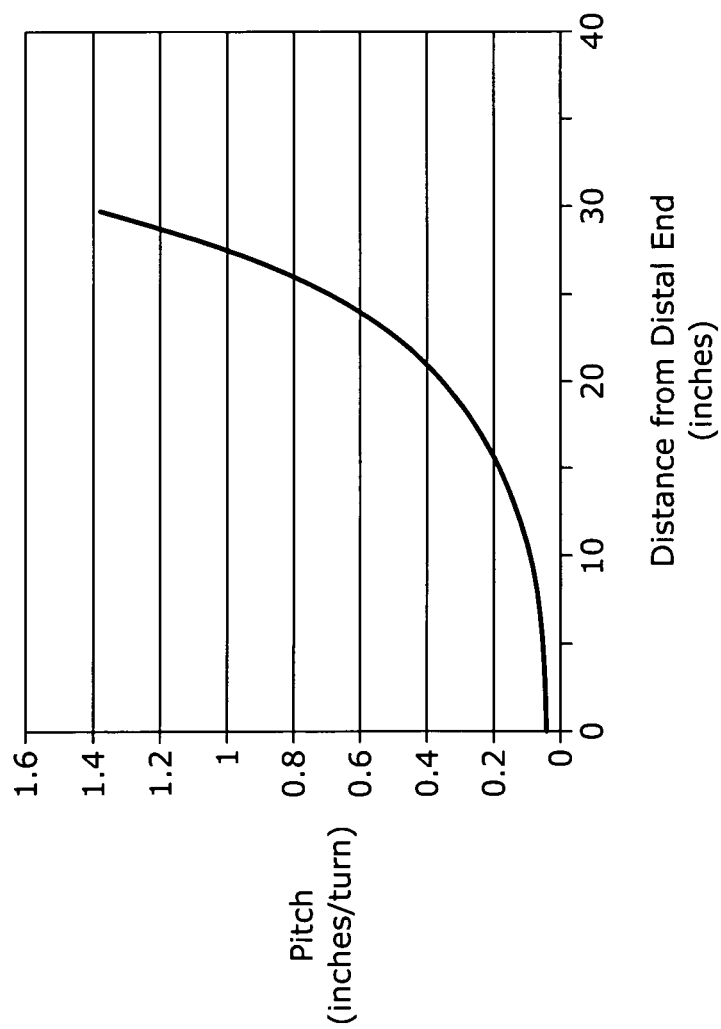
FIG. 8 is a graphical representation illustrating an exponentially decaying pitch in accordance with an embodiment of the invention.

FIG. 7 illustrates several additional possible exponential pitches in which A is set equal to 0.0192, B varies from 0.07 to 0.14, and C is set equal to zero. FIG. 8 illustrates a particular exponential pitch in which A is set equal to 0.0192, B is set equal to 0.1425, and C is set equal to zero. It can be seen that the pitch, or inches per turn, increases rapidly in moving from the distal end to the proximal end of the intermediate metallic layer 36.

Figure 9:
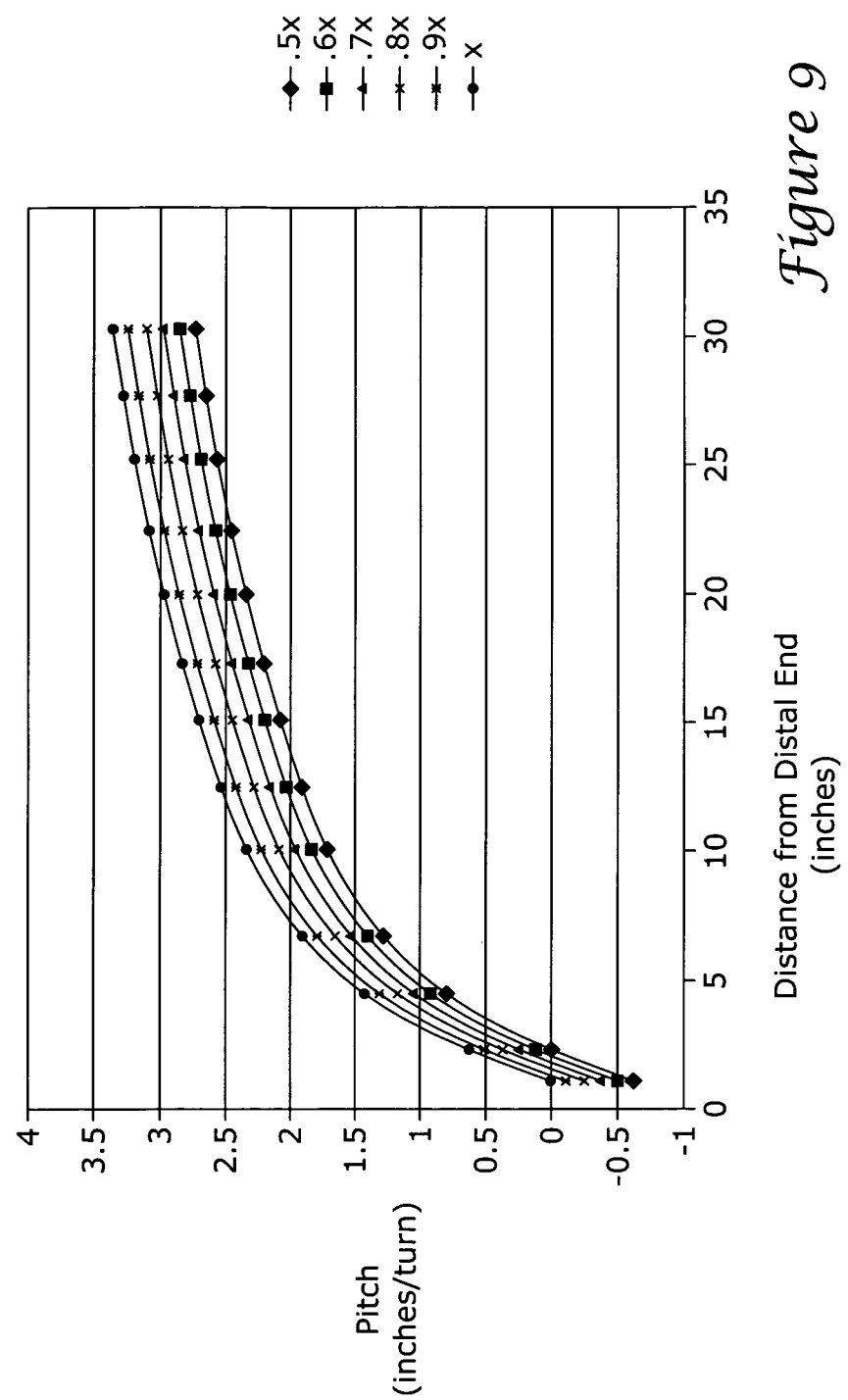
FIG. 9 is a graphical representation illustrating examples of logarithmic decaying pitch.

In some embodiments, the pitch may decrease logarithmically when moving toward the distal end 28. In some embodiments, the pitch may be given by the formula $y=A+B \ln Cx$, where y is the pitch, x is the distance from the distal end of the elongate shaft 24, A is in a range of about 0 to about 25, B is in a range of about 0.5 to about 25, and C is in a range of about 0.5 to about 100. FIG. 9 illustrates several possible logarithmic pitches in which A is set equal to zero, B is set equal to 1, and C varies from 0.5 to 1.0. It can be seen that the pitch, or inches per turn, increases rapidly in moving from the distal end to the proximal end of the intermediate metallic layer 36.

Figure 10:
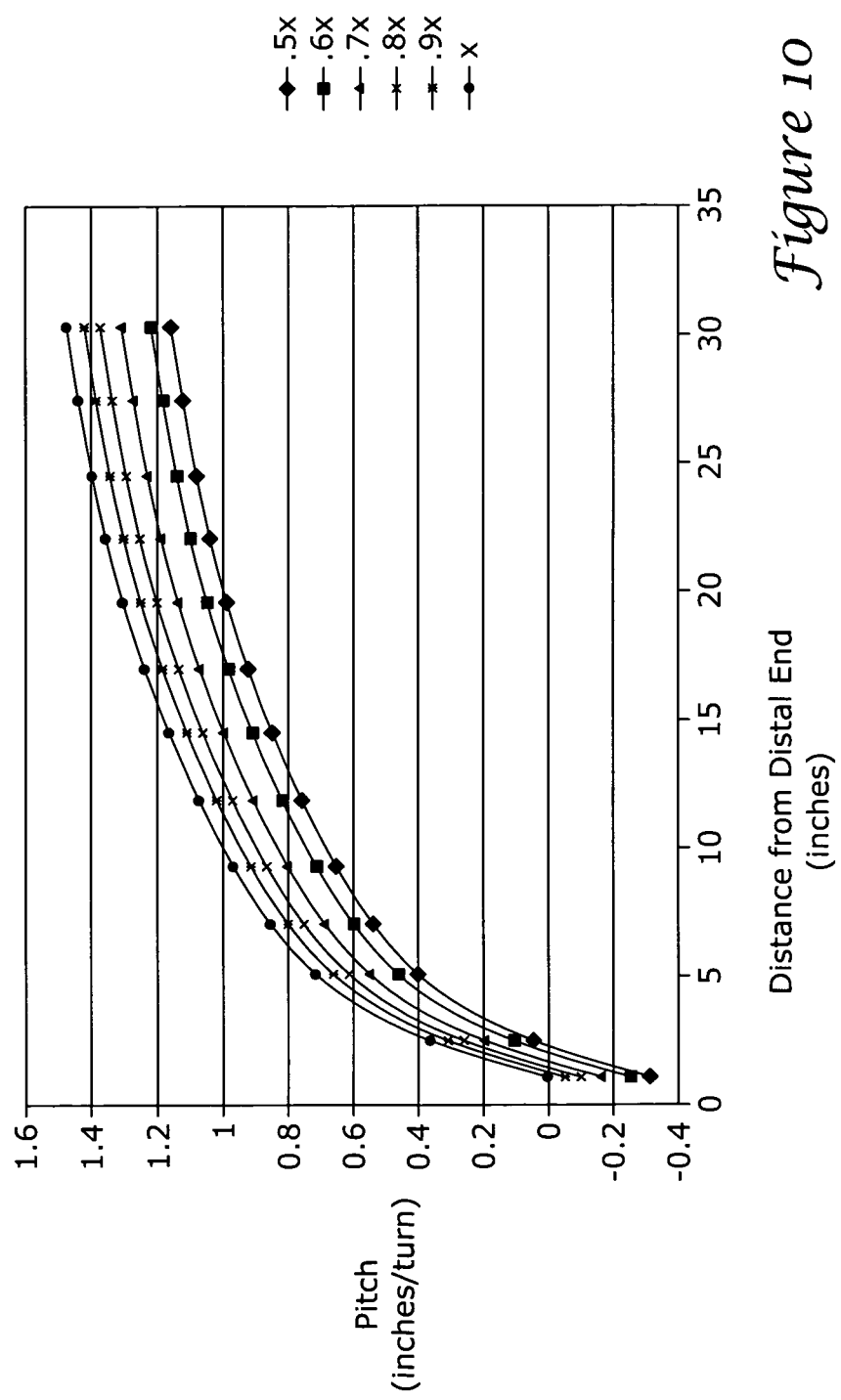
FIG. 10 is a graphical representation illustrating examples of base 10 logarithmic decaying pitch.

In some embodiments, the pitch may be given by the formula $y=A+B \log Cx$, where y is the pitch, x is the distance from the distal end of the elongate shaft 24, A is in a range of about 0 to about 100, B is in a range of about 20 to about 200, and C is in a range of about 0.01 to about 100. FIG. 10 illustrates several possible logarithmic pitches in which A is set equal to zero, B is set equal to 1, and C varies from 0.5 to 1.0. It can be seen that the pitch, or inches per turn, increases rapidly in moving from the distal end to the proximal end of the intermediate metallic layer 36.

In some instances, the pitch may be a second power pitch, a third power pitch or a fourth power pitch, and may be given by the formula $y=Ax^2+Bx+C$, where y is the pitch, x is the distance from the distal end of the elongate shaft 24, A is in the range of about 0.001 to about 0.5, B is in the range of about 0 to about 0.001, C is in the range of about 0 to about 100.

Figure 11:
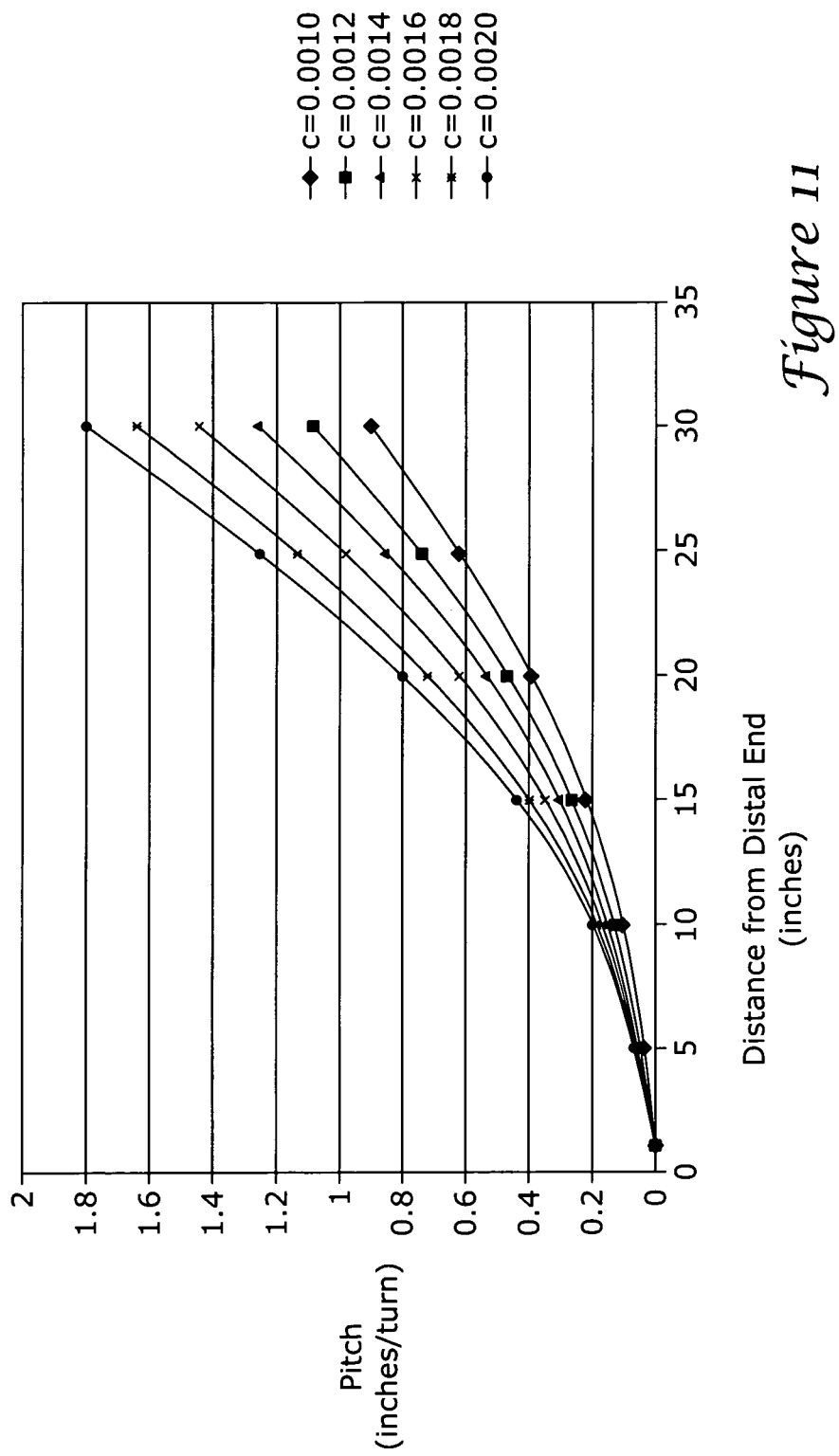
FIG. 11 is a graphical representation illustrating examples of second power decaying pitch in accordance with an embodiment of the invention.
Figure 12:
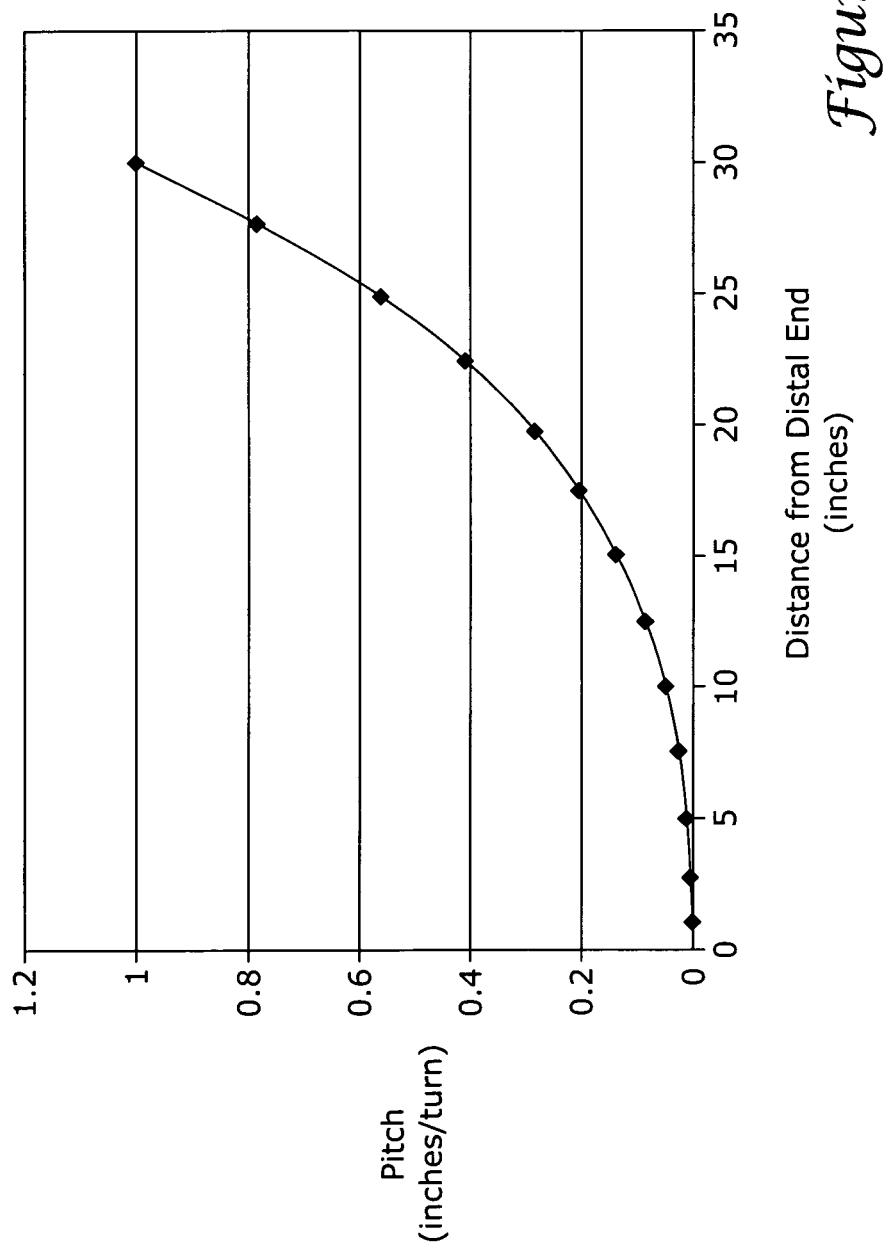
FIG. 12 is a graphical representation illustrating an example of third power decaying pitch in accordance with an embodiment of the invention.

FIG. 11 illustrates several possible pitches in which A and B are set equal to zero, C varies from 0.001 to 0.002, and D and E are each set equal to zero. FIG. 12 illustrates a possible pitch in which A, C, D and E are each set equal to zero and B is set equal to $3.7 \times 10^{-5}$. In each case, it can be seen that the pitch, or inches per turn, increases rapidly in moving from the distal end to the proximal end of the intermediate metallic layer 36.

One of skill will recognize that a number of other equations may also be used to determine pitch as a function of distance from a distal end. In each of the illustrative but non-limiting examples provided herein it should be noted that the pitch is a function of distance from the distal end. Moreover, in each of these examples, the rate at which the pitch changes, or the first derivative of the pitch, is also a function of relative position.

Figure 13:
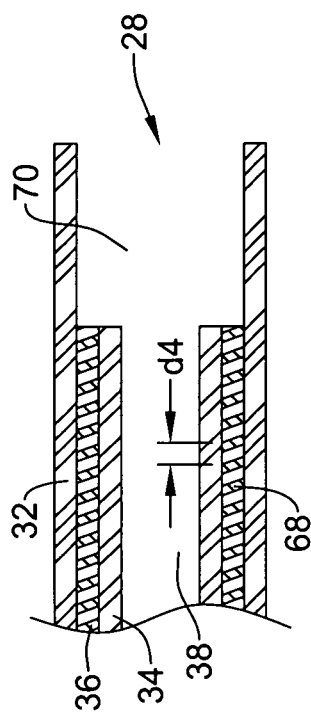
FIG. 13 is a longitudinal cross-section taken at the distal end of FIG. 2.

Returning now to FIG. 2, it can be seen that FIG. 13 is a longitudinal cross-section taken near the distal end 28 of the elongate shaft 24. In FIG. 13, it can be seen that the intermediate metallic layer 36 includes a relatively larger number of spiral cuts 68 that are spaced apart a distance d4. In comparing FIG. 13 to FIG. 4, it can be seen that in FIG. 13 (representing the distal end of the elongate shaft 24), the spiral cuts 68 are much more numerous and are much closer together than anywhere else along the elongate shaft 24. As discussed above, a larger number of closely-spaced spiral cuts near the distal end 28 provides improved flexibility at the distal end 28.

Figure 16:
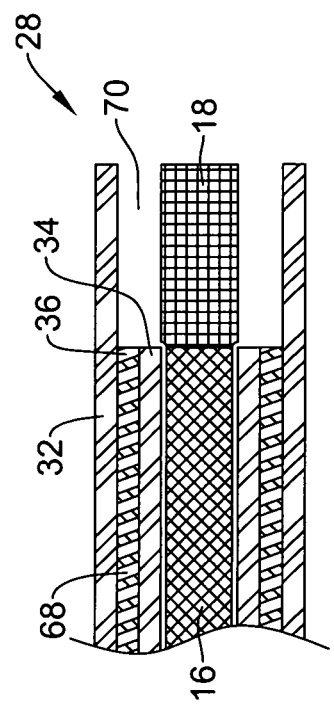
FIG. 16 is a longitudinal cross-section taken at the distal end of FIG. 14.

In FIG. 13, it can be seen that the outer polymer layer 32 extends to the distal end 28 while the inner polymer layer 34 and the intermediate metallic layer 36 both stop at a position that is proximal to the distal end 28. This permits the lumen 38 to widen into a transducer volume 70. As previously discussed, the lumen 38 may accommodate an ultrasound drive shaft. The transducer volume 70 may be sized to accommodate an ultrasound transducer, as illustrated in FIGS. 14-16.

Figure 14:
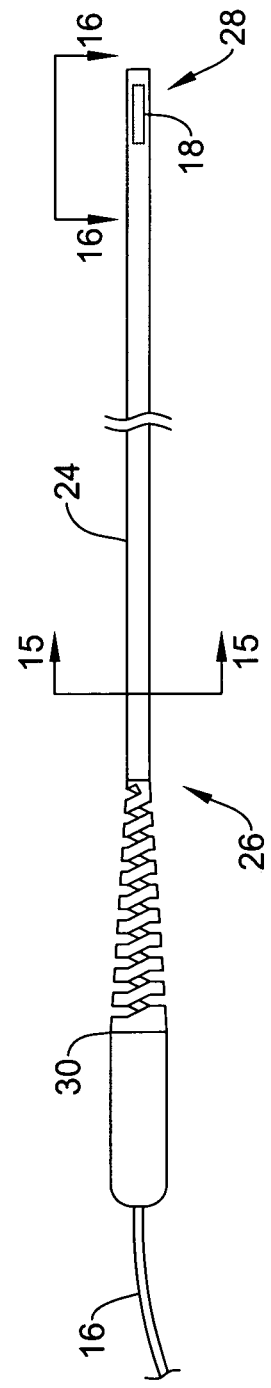
FIG. 14 is a schematic illustration of the intravascular ultrasound catheter of FIG. 2, shown including a drive shaft positioned within the catheter.
Figure 15:
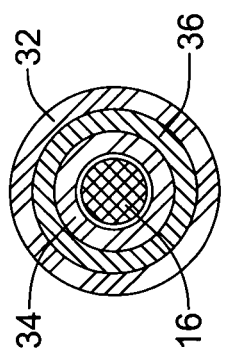
FIG. 15 is a cross-section taken along line 15-15 of FIG. 14.

FIG. 14 is a schematic view of the intravascular ultrasound catheter 12 in which drive shaft 16 has been inserted through the lumen 38 such that the ultrasound transducer 18 (seen in phantom in FIG. 14) is positioned near the distal end 28. FIG. 15 is a cross-sectional view taken along line 15-15 of FIG. 14 showing the drive shaft 16 positioned within the lumen 38 while FIG. 16 is a longitudinal cross-section taken at the distal end of FIG. 14 illustrating placement of the transducer 18 within the transducer volume 70.

In some embodiments, part or all of the catheter 12 may include a lubricious coating. Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding and solubility. In some embodiments, a distal portion of the catheter can be coated with a hydrophilic polymer, while the more proximal portions can be coated with a fluoropolymer.

The invention should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

What I claim is:

1. An intravascular ultrasound catheter having a distal portion and a proximal portion, the catheter comprising:
    an inner polymeric layer, the inner polymeric layer having a plurality of apertures formed therein;
    an outer polymeric layer; and
    a spiral-cut hypotube, the spiral-cut hypotube positioned between the inner polymeric layer and the outer polymeric layer and extending from the distal portion to the proximal portion of the catheter, the spiral-cut hypotube having a distal end;
    wherein the spiral-cut hypotube has a pitch having a rate of change that is dependent upon a distance from the distal end of the hypotube.

2. The intravascular ultrasound catheter of claim 1, wherein the pitch is determined by a formula having a first derivative that is a function of the distance from the distal end of the hypotube.

3. The intravascular ultrasound catheter of claim 1, wherein the spiral-cut hypotube has an exponential pitch.

4. The intravascular ultrasound catheter of claim 1, wherein the spiral-cut hypotube has a pitch given by the formula $y=A^{(Bx)}+C$, where y is the pitch, x is the distance from the distal end of the hypotube, A is in a range of about 5 to about 100, B is in a range of about 0.01 to about 1, and C is in a range of about 0 to about 25.

5. The intravascular ultrasound catheter of claim 1, wherein the spiral-cut hypotube has a logarithmic pitch.

6. The intravascular ultrasound catheter of claim 1, wherein the spiral-cut hypotube has a pitch given by the formula $y=A+B \ln Cx$, where y is the pitch, x is the distance from the distal end of the hypotube, A is in a range of about 0 to about 25, B is in a range of about 0.5 to about 25, and C is in a range of about 0.5 to about 100.

7. The intravascular ultrasound catheter of claim 1, wherein the spiral-cut hypotube has a pitch given by the formula $y=A+B \log Cx$, where y is the pitch, x is the distance from the distal end of the hypotube, A is in a range of about 0 to about 100, B is in a range of about 25 to about 200, and C is in a range of about 0.01 to about 100.

8. The intravascular ultrasound catheter of claim 1, wherein the spiral-cut hypotube has a second power pitch.

9. The intravascular ultrasound catheter of claim 1, wherein the spiral-cut hypotube has a pitch given by the formula $y=Ax^2+Bx+C$, where y is the pitch, x is the distance from the distal end of the hypotube, A is in the range of about 0.001 to about 5, B is in the range of about 0 to about 0.001, C is in the range of about 0 to about 100.

10. The intravascular ultrasound catheter of claim 1, wherein the inner polymeric layer defines a lumen adapted to accommodate an intravascular ultrasound drive shaft and transducer.

11. The intravascular ultrasound catheter of claim 1, wherein at least one of the outer polymeric layer and the inner polymeric layer extends distally from the distal end of the spiral-cut hypotube.

12. An intravascular ultrasound catheter having a distal portion and a proximal portion, the catheter comprising:
    an inner polymeric layer;
    an outer polymeric layer;
    a spiral-cut hypotube, the spiral-cut hypotube positioned between the inner polymeric layer and the outer polymeric layer and extending from the distal portion to the proximal portion of the catheter, the spiral-cut hypotube having a distal end;
    wherein the spiral-cut hypotube has a pitch having a rate of change that is dependent upon a distance from the distal end of the hypotube; and
    wherein the spiral-cut hypotube comprises a machined kerf, and the inner polymeric layer comprises a plurality of apertures in fluid communication with the machined kerf.

13. The intravascular ultrasound catheter of claim 12, wherein the outer polymeric layer comprises a plurality of apertures in fluid communication with the machined kerf.

14. An intravascular ultrasound assembly, comprising:
an intravascular ultrasound drive shaft having a distal end;
an ultrasound transducer positioned near the distal end of the drive shaft; and
a catheter adapted to receive the ultrasound drive shaft, the catheter comprising:
   an inner polymeric layer, the inner polymeric layer defining a lumen adapted to accommodate the intravascular ultrasound drive shaft;
   an outer polymeric layer; and
   a spiral-cut hypotube positioned between the inner polymeric layer and the outer polymeric layer and extending from a distal portion to a proximal portion of the catheter, the spiral-cut hypotube having a distal end.

15. The intravascular ultrasound assembly of claim 14, wherein at least one of the outer polymeric layer and the inner polymeric layer extends distally from the distal end of the spiral-cut hypotube.

16. The intravascular ultrasound assembly of claim 14, wherein the spiral-cut hypotube has a pitch defining distance between adjacent turnings.

17. The intravascular ultrasound assembly of claim 16, wherein the pitch varies as a function of distance from the distal end of the spiral-cut hypotube.

18. The intravascular ultrasound assembly of claim 16, wherein the pitch has a rate of change that is a function of distance from the distal end of the spiral-cut hypotube.

19. The intravascular ultrasound assembly of claim 16, wherein the spiral-cut hypotube has an exponential pitch given by the formula $y=A^{(Bx)}+C$, where y is the pitch, x is a distance from the distal end of the hypotube, A is in a range of about 5 to about 100, B is in a range of about 0.01 to about 1, and C is in a range of about 0 to about 25.

20. The intravascular ultrasound assembly of claim 16, wherein the spiral-cut hypotube has a logarithmic pitch given by the formula $y=A+B \ln Cx$, where y is the pitch, x is a distance from the distal end of the hypotube, A is in a range of about 0 to about 25, B is in a range of about 0.5 to about 25, and C is in a range of about 0.5 to about 100.

21. The intravascular ultrasound assembly of claim 16, wherein the spiral-cut hypotube has a logarithmic pitch given by the formula $y=A+B \log Cx$, where y is the pitch, x is a distance from the distal end of the hypotube, A is in a range of about 0 to about 100, B is in a range of about 25 to about 200, and C is in a range of about 0.01 to about 100.

22. The intravascular ultrasound assembly of claim 16, wherein the spiral-cut hypotube has a pitch given by the formula $y=Ax^2+Bx+C$, where y is the pitch, x is a distance from the distal end of the hypotube, A is in the range of about 0.001 to about 5, B is in the range of about 0 to about 0.001, C is in the range of about 0 to about 100.

* * * * *